United States Patent [19]

McAteer et al.

[11] Patent Number: 5,780,635
[45] Date of Patent: Jul. 14, 1998

US005780635A

[54] PYRIDINE BASE SYNTHESIS

[75] Inventors: Colin Hugh McAteer; Douglas Clifford Brown, both of Indianapolis; Robert Drummond Davis, Sr., Greencastle, all of Ind.

[73] Assignee: Reilly Industries, Inc., Indianapolis, Ind.

[21] Appl. No.: 668,580

[22] Filed: Jun. 21, 1996

Related U.S. Application Data

[60] Provisional application No. 60/000,470, Jun. 23, 1995.
[51] Int. Cl.$^6$ .................... C07D 213/09; C07D 213/10
[52] U.S. Cl. ........................................ 546/251; 546/250
[58] Field of Search ................................ 546/250, 251

[56] References Cited

U.S. PATENT DOCUMENTS

| | | | |
|---|---|---|---|
| 3,020,280 | 2/1962 | Cislak et al. | 546/181 |
| 3,020,281 | 2/1962 | Cislak et al. | 546/181 |
| 3,020,282 | 2/1962 | Cislak et al. | 546/181 |
| 3,308,069 | 3/1967 | Wadlinger et al. | 252/455 |
| 4,016,218 | 4/1977 | Haag et al. | 585/467 |
| 4,220,783 | 9/1980 | Chang et al. | 546/251 |
| 4,388,461 | 6/1983 | Chang et al. | 546/251 |
| 4,518,485 | 5/1985 | LePierre et al. | 208/89 |
| 4,628,097 | 12/1986 | Le Blanc et al. | 546/251 |
| 4,675,410 | 6/1987 | Feitler et al. | 546/251 |
| 4,714,537 | 12/1987 | Jorgensen et al. | 208/111 |
| 4,810,794 | 3/1989 | Shimizu et al. | 546/251 |
| 4,861,894 | 8/1989 | Bowes et al. | 546/251 |
| 4,866,179 | 9/1989 | Cheng et al. | 546/250 |
| 4,910,006 | 3/1990 | Zones et al. | 423/328 |
| 5,013,843 | 5/1991 | Feitler et al. | 546/251 |
| 5,164,169 | 11/1992 | Rubin | 423/709 |
| 5,218,122 | 6/1993 | Goe et al. | 546/251 |
| 5,304,698 | 4/1994 | Husain | 585/722 |
| 5,395,940 | 3/1995 | Angevine et al. | 546/250 |

FOREIGN PATENT DOCUMENTS

| | | | |
|---|---|---|---|
| 0289924A2 | 11/1988 | European Pat. Off. | C07D 213/08 |
| 0382543A2 | 8/1990 | European Pat. Off. | C07D 213/10 |
| 3634259A1 | 4/1988 | Germany | C07D 213/12 |
| 8202884 | 2/1984 | Netherlands | C07D 13/09 |
| 1235390 | 6/1971 | United Kingdom | |
| WO90/03366 | 4/1990 | WIPO | C07D 213/09 |

OTHER PUBLICATIONS

Frillette, V.J., Haag, W.O., Lago, R.M., Catalysis By Crystalline Aluminosilicates: Characterization of Intermediate Pore-Size Zeolites by the "Constraint Index". *J. of Catalysis*, vol. 67, pp. 218–222 (1981).

Haggin, J., "New Zeolite Structures Promising For Catalysis", C & En. p. 8, Dec. 6, 1993.

Higgins, J.B., LaPierre, R.B., Schlenker, J.L., Rohrman, A.C., Wood, J.D., Kerr, G.T. Rohrbaugh, W.J., "The Framework Topology Of Zeolite Beta", *Zeolites*, vol. 8, pp. 446–452, Nov. 1988.

Lobo, R.F., Pan, M., Chan, I., Li, H–X., Medrud, R.C., Zones, S.I., Crozier, P.A., Davis, M.E., "SSZ–26 And SSZ–33: Two Molecular Sieves With Intersecting 10–And 12–Ring Pores", *Science*, vol. 262, pp. 1543–1546, Dec. 3, 1993.

Weitkamp, J., Ernst, S., Kumar, R., "The Spaciousness Index: A Novel Test Reaction For Characterizing The Effective Pore Width Of Bifunctional Zeolite Catalysts", *Applied Catalysis*, vol. 27, pp. 207–210 (1986).

Weitkamp, J., Chen, C.Y., Ernst, S., "Characterization Of Zeolites By The Spaciousness Index", *Successful Design of Catalysts*, pp. 343–350 (1988).

*Primary Examiner*—Alan L. Rotman
*Attorney, Agent, or Firm*—Woodard, Emhardt, Naughton, Moriarty & McNett

[57] ABSTRACT

A base synthesis process and catalyst for the preparation of pyridine or its alkylpyridine derivatives involving the catalytic reaction of one or more aldehydes and/or ketones containing from one to about five carbon atoms, with at least one reactant having more than one carbon atom, with ammonia in the gas phase. The catalyst comprises an effective amount of a large-pore zeolite having been prepared with a silica to alumina ratio of at least 15, and at least a first dimension having first channels formed by twelve-membered rings, and a second dimension having second channels formed by ten- or twelve-membered rings which intersect the first channels. The preferred zeolite is a zeolite having the structure of zeolite beta.

25 Claims, No Drawings

PYRIDINE BASE SYNTHESIS

CROSS-REFERENCE

This application claims priority upon provisional U.S. patent application Ser. No. 60/000,470, filed Jun. 23, 1995.

BACKGROUND OF THE INVENTION

This invention relates to a process for pyridine base synthesis utilizing large pore zeolite catalysts, and to novel modified large pore zeolite catalysts particularly useful for pyridine base synthesis.

The term "base synthesis" is known and used in the pyridine field and in this application to identify a process by which bases of pyridine or alkylpyridine derivatives are prepared by reacting aldehydes and/or ketones with ammonia in the gas phase using a heterogeneous catalyst. Some examples of base synthesis reactions (and their common names where appropriate) include: the synthesis of pyridine and beta-picoline from acetaldehyde and formaldehyde (the "pyridine-beta reaction"); the synthesis of alpha- and gamma-picoline from acetaldehyde (the "alpha-gamma reaction"); the synthesis of 2,6-dimethylpyridine ("2,6-lutidine") from acetone and formaldehyde; the synthesis of 2,4,6-trimethylpyridine ("sym-collidine") from acetone alone or with acetaldehyde; the synthesis of pyridine and beta-picoline from acrolein alone or with acetaldehyde; the synthesis of 3,5-dimethylpyridine from propionaldehyde and formaldehyde; and the synthesis of beta-picoline from acetaldehyde, formaldehyde and propionaldehyde. Many others are known and reported or practiced in the art, and are equally considered within the scope of the description and invention herein.

The catalysts used in these pyridine base synthesis reactions have included alumina which was used early-on either alone or as a support for zinc fluoride or other metal salts, as well as an amorphous structure incorporating both silica and alumina which became an important commercial catalyst. See U.S. Pat. Nos. 2,807,618 and 2,744,904; and German Patent No. 1,255,661. Similarly, the reactor designs for these heterogeneous gas-phase reactions have varied within the basic categories of fixed-bed and fluid-bed forms. The advantages of fluidized beds were recognized early-on (see U.S. Pat. No. 2,807,618) as evidenced by the fact that the early commercial-scale base synthesis units used fluidized beds, and that most units brought into operation since then incorporate fluidized catalyst beds. One reason for this is that base synthesis reactions always produce deposits of dark, mostly carbonaceous materials referred to as "coke" which tend to foul the catalyst thereby gradually reducing its activity. Although variations are observed, all catalysts accumulate these coke deposits at an appreciable rate such that periodic action is required. As discarding catalyst is not desirable for economic reasons, regeneration by heating in air or other oxygen-containing gases is commonly employed. This regeneration/combustion process is very exothermic and also best carried out in a fluid bed process. C. L. Thomas, "Catalytic Processes and Proven Catalysts", Academic Press, New York, pp. 11–14 (1970).

Accordingly, a common technique has long been to run two fluid beds concurrently, one for reaction and one for regeneration, with catalyst continuously or intermittently cycled between the beds. Operating parameters such as circulation rates, contact times, temperatures and the like are readily determined by skilled operators in view of the specific reactions and/or ingredients used. See, e.g., German Patent No. 2,203,384. An ancillary benefit of this technique is that product yields from base synthesis reactions carried out in fluidized beds are recognized to be generally higher than in corresponding fixed-bed reactions. This was emphasized in two families of patents issued to BP Chemicals U.K. Ltd. of London, England, one for alpha-gamma synthesis (British Patent No. 1,188,891; German Patent 1,903,879; and Canadian Patent No. 852,745) and the other for, pyridine-beta synthesis (British Patent No. 1,235,390; Canadian Patent No. 851,727; and German Patent No. 1,903,878). These BP patents, and German Patent No. 1,903,878 in particular, compare fixed- and fluid-bed reactions using catalysts of amorphous silica-alumina or of metal compounds such as the oxides or fluorides of lead, zinc and cadmium on amorphous silica-alumina supports.

This same advantage of fluid-bed usage was reported by Feitler et al. in U.S. Pat. No. 4,675,410 for base synthesis catalysts composed of shape-selective aluminosilicates (commonly referred to as "zeolites") used in their acidic form. These crystalline zeolites had earlier been reported for base synthesis reactions by Chang et al. in U.S. Pat. No. 4,220,783 both in their acid- or H-form and as ion-exchanged with cadmium, copper or nickel. Several examples in the Chang patent demonstrated deactivation of the catalyst over time thereby also suggesting the desirability of a fluid-bed to reactivate the catalyst by heating in air in any commercial application.

In general, these base synthesis reactions have received universal acceptance as evidenced by their continuous commercial use for many years. The products of base synthesis, including pyridine, alpha-, beta- and gamma-picoline, nearly all the lutidines, and primarily the symmetrical isomer of collidine, have all shown commercial importance in the world chemical market albeit of varying values and volume requirements. See Goe, "Pyridine and Pyridine Derivatives," Encyclopedia of Chemical Technology, Vol. 19, 3rd. Ed. (1982). It is also the case that improvement in the yields of these reactions and variation in their product ratios may be desirable according to market trends for such pyridine-derivative products as the herbicide paraquat, vitamins such as niacin and niacinamide, tire cord adhesive derived from 2-vinylpyridine, the tuberculosis drug Isoniazid, and so forth. One approach to this end has examined variations in reaction conditions such as temperature, velocity or contact time, mole ratios of feed stocks, and the like. Here, optimization of yield or product ratio is generally accomplished by known techniques employed by those skilled in this area. A second approach has involved catalyst variation in which far less predictability exists.

For example, while work early-on was with amorphous silica-alumina or other catalysts, the concentration in recent years has shifted to so-called shape-selective zeolites which are aluminosilicates of definite crystal structure having activities and pores of a size similar to that of other commercially-interesting molecules. See, e.g., E. G. Derouane, "New Aspects of Molecular Shape-Selectivity: Catalysis by Zeolite ZSM-5", Catalysis by Zeolites, ed. B. Imelik et al., Elsevier, Amsterdam. pp. 5–18 (1980). Generally speaking, zeolites include a three-dimensional lattice of $SiO_4$ tetrahedra crosslinked by sharing of oxygen atoms. Optionally, zeolites can include other atoms in the lattice, for example aluminum in the form of $AlO_4$ tetrahedra. The structure of zeolites is determinative of the ingress and egress of chemicals into and from internal spaces in the zeolites. This structure includes pores defined by rings which are formed by the regular disposition of the tetrahedra making up the anionic framework of the crystalline aluminosilicate, the oxygen atoms being bonded to the silicon or aluminum atoms at the centers of the tetrahedra. Both the size of the rings (i.e. the number of tetrahedral atoms or members included in the rings) and their conformation are primary contributers to the accessability to and from interior spaces of the zeolites. Large pore zeolites are generally understood to have pores defined by at least twelve-membered rings, medium pore zeolites to have pores defined by ten-membered rings (but none by twelve-membered rings), and small pore zeolites to have pores defined by no larger than eight-membered rings.

These zeolite materials are often defined by a constraint index which is an experimentally-derived number based on the observed relative rates of reaction of straight- and branched-chain molecules. Frillette et al., J. Catal., 67, 218 (1981). The term "zeolite" has even acquired a broader meaning in the art, and is accordingly used in this application to mean more than the original crystalline aluminosilicate materials. For example, "zeolite" is understood and meant to also include compositions such as gallosilicates, ferrosilicates, chromosilicates and borosilicates. Crystalline aluminum phosphates ("ALPO's") and silicon-aluminum phosphates ("SALPO's") are also included in its coverage because of their catalytic ability, as is even theoretically-pure crystalline silicalite such as a S-115 material marketed by Union Carbide Corporation of New York.

In these zeolite materials, some ion-exchange properties are generally thought to exist due to positive ions associated with the trivalent molecular centers (e.g., aluminum, boron, gallium, etc.) that are present in the network of tetravalent silicon centers. Although ALPO is an exception to this, and silicalite may be an exception but for residual aluminum in its crystal structure, it has also been thought that catalytic activity is associated somehow with these ion-exchange sites. As synthesized, zeolites typically have sodium and quaternary ammonium ions in their crystal structures. These synthesized materials can be heated to convert them to a form containing sodium and $H^+$ ions. If the sodium ions are then exchanged for ammonium ($NH4^+$) ions and the resulting ammonium zeolite heated, an acidic or "H-form" zeolite results with these acid centers believed to be associated with some catalytic activity. For instance, an H-form of ZSM-5 zeolite is marketed by The Mobil Corporation of New York and is used in the synthesis of gasoline from methanol.

One approach at optimizing yield and/or product ratios from base synthesis reactions has been to stress maximizing these acidic sites. For example, the Feitler patent claims the specific benefit of a higher ratio of pyridine in the pyridine-beta synthesis by use of a zeolite catalyst of preferably 80–100% this H-form although no direct comparison with other ion-exchanged zeolites is reported.

Other positive ions have also been exchanged for the sodium, ammonium or H-sites in the zeolite structure. For example, cracking catalysts have used a rare earth ion-exchanged form of the large-pore zeolite Y (called "REY"). C. L. Thomas, "Catalytic Processes and Proven Catalysts", supra, pp. 30–31. Precious metals have been exchanged in both large-pore and shape-selective zeolites to produce reforming catalysts. E.G. Derouane, "New Aspects of Molecular Shape-Selectivity: Catalysis by Zeolite ZSM-5", supra, p. 17. The Chang patent also reported use of zeolites ion-exchanged with cadmium, copper or nickel ions in addition to the H-form of Mobil's ZSM-5 material in base synthesis reactions. The Chang patent did test the catalytic activity of these metal ion-forms, but did not speculate on whether they existed solely or survived in their ionic state or were reduced to base metals.

Shimizu et al. described base synthesis reactions using shape-selective zeolites treated with thallium, lead or cobalt ions or compounds in an European application, Serial No. 232,182 published Aug. 12, 1987. These metals were ion-exchanged into a zeolite of alkali, ammonium or acid form in an aqueous medium or were mixed in the solid state with no apparent effect from the mode of mixing used. As in the Feitler patent, Shimizu also reported the desire for a low yield of beta-picoline from pyridine-beta base synthesis. However, this work does not permit direct comparison with Feitler as Shimizu used a reaction mixture with so little formaldehyde (0.5 moles per mole of acetaldehyde) that it necessarily produced about equal amounts of beta- and gamma-picoline which are of questionable commercial utility. See, e.g., Beschke, Ullmann Encyclopedia, p. 593 (1980).

It is in the light of this background, and of the large body of general chemical literature concerned with base synthesis processes (see F. Brody and P. R. Ruby, Pyridine and Its Derivatives, E. Klingsberg ed., Vol. 1 (1960); N. S. Boodman et al., Ibid, Supplement Abramovitch ed., Vol. 1 (1975); T. D. Bailey, G. L. Goe and E. F. V. Scriven, Ibid, Supplement G. R. Newkome ed., Vol. 5 (1984)), that the applicants approached this study with the objectives of providing new pyridine base syntheses which employ heterogeneous catalysts which are readily and relatively inexpensively available, and in which catalyst activity is maintained at a consistent level over extended periods of time.

SUMMARY OF THE INVENTION

A feature of the present invention is the surprising discovery that certain large pore zeolites, when used in the pyridine base synthesis reaction, give high yields of useful pyridine bases over extended periods of time. This discovery directly contrasts reports in the literature of relatively poor results with large pore zeolites when used as catalysts in the pyridine base synthesis (see, e.g. H. Sato et al., *Chem. Lett.*, 1994, 59 and U.S. Pat. No. 4,810,794) and is contrary to the current shift in industry and the literature to the use of medium pore zeolites in the pyridine base synthesis. Accordingly, one preferred embodiment of the present invention provides a base synthesis process for preparing pyridine or its alkyl pyridine derivatives, which includes reacting one or more aldehydes and/or ketones or mixtures thereof containing from 1 to about 5 carbon atoms, with at least one reactant having more than 1 carbon atom, with ammonia in the gas phase and in the presence of an effective amount of a large pore zeolite catalyst having a silica to alumina molar ratio of at least 15. In accordance with the invention the selected zeolite further has a first dimension having first channels formed from twelve-membered rings, and a second dimension having second channels intersecting the first channels and formed from ten-membered or twelve-membered rings. Preferred catalysts for use in the invention also have a third dimension having third channels preferably intersecting the first and second channels and formed by ten- or twelve-membered rings. Zeolites having the structure of zeolite beta exhibit such a three-dimensional structure and are preferred catalyst materials for use in the present invention. The catalysts used in processes of the invention can be but are not necessarily modified to incorporate one or more metals, for example to serve to promote the formation of pyridine bases. In use, the catalysts can be employed in fixed bed or moving bed (e.g. fluidized bed) reactor systems as commonly employed in the pyridine field, in a broad array of pyridine base synthesis processes for the production of pyridine itself and/or alkylpyridines. In addition, the selected catalysts of the invention can be employed alone or in combination with other catalysts including large, medium or small pore zeolite catalysts. As is generally known, for use in the pyridine base synthesis, these zeolite catalysts will typically be formulated with a naturally-occurring or synthetic binder material such as a clay, silica, alumina, silica-alumina, and the like. The bound zeolite catalyst is thereby put into a physical form preferred for use in the fixed or fluidized beds commonly used in industry.

In another embodiment, the present invention provides a set of modified, large pore zeolite catalysts which have proven to be particularly advantageous in promoting the formation of pyridines or alkylpyridines in the pyridine base synthesis. These catalyst materials of the invention include select large pore zeolites of the type disclosed above, which have been modified to incorporate metal ions to result in catalysts which provide improved results in the pyridine base synthesis reaction. Preferred catalysts of this embodiment of the invention incorporate one or more metals selected from the group lead, cobalt, tin, cadmium, gallium, thallium and platinum.

The present invention provides pyridine base synthesis processes for preparing pyridine and/or alkylpyridines which employ large pore zeolite catalysts such as zeolite beta which are readily available to the user, and which surprisingly and in contrast to trends both in the literature and industry provide processes in which relatively high yields and productivities for useful pyridine bases are achieved, and are furthermore maintained over extended periods of catalyst use thus evidencing minimal degeneration of catalyst activity. Further objects, features, advantages and embodiments of the invention will become apparent from the following description and the appended claims.

DESCRIPTION OF THE PREFERRED EMBODIMENTS

For the purposes of promoting an understanding of the principles of the invention, reference will now be made to certain embodiments thereof and specific language will be used to describe the same. It will nevertheless be understood that no limitation of the scope of the invention is thereby intended, such alterations and further modifications of these embodiments, and such further applications of the principles of the invention as described herein being contemplated as would normally occur to one skilled in the art to which the invention relates.

As disclosed above, one preferred embodiment of the present invention relates to the discovery of a new base synthesis process for the preparation of pyridine or its alkylpyridine derivatives involving the catalytic reaction of one or more aldehydes and/or ketones containing from one to about five carbon atoms, with at least one reactant having more than one carbon atom, with ammonia in the gas phase. The reaction is carried out in the presence of an effective amount of a selected, large pore zeolite, as broadly defined above, which has optionally been modified so as to incorporate one or more metals.

The preferred zeolite for use in the present invention is one which is formed having a silica to alumina molar ratio of at least about 15, and exhibits at least a two-dimensional porous microstructure, wherein a first dimension has first channels formed by twelve-membered rings, and a second dimension has second channels which intersect the first channels and which are formed by rings having at least ten members, commonly being ten- or twelve-membered rings. More preferred catalysts for use in the present invention exhibit a three-dimensional pore structure, with the first two dimensions being configured as discussed above, and the third dimension having channels formed by ten- or twelve-membered rings, and preferably intersecting the first and second channels. Most preferred zeolite catalysts for use in the invention have a three-dimensional pore structure such as that of zeolite beta, wherein each dimension has channels formed by twelve-membered rings and wherein the channels each intersect one another.

A preferred group of zeolites for use in the invention may be further characterized by having a constraint index typical of large pore zeolites, for example less than 1 and commonly falling in the range of about 0.1 to 0.9. In this regard, this "constraint index" is a conventional term which is well-known and used in the art to characterize porous catalyst materials including zeolites, and as used herein refers to the value as determined in the conventional fashion which is described for example in Frillette et al, Journal of Catalysis, 67, 218–222 (1981). As an alternative or additional characterization to the constraint index, preferred catalysts for use in the invention also have "spaciousness indexes" greater than about 5, for example in the range of about 5–25, more preferably about 10–20, determined as described in Weitkamp et al., *App. Catal.* 27, 207–210 (1986).

The preferred zeolite will also have been initially prepared having a relatively high silica to alumina molar ratio, for instance falling in the range of about 15 to about 90, and more preferably falling in the range of about 20 to about 80. In this regard, this stated silica to alumina ratio characterizes the zeolite at its initial preparation, and thus does not take into account post-formation treatments, for example steaming, which can remove alumina from the zeolite framework and thus alter the silica to alumina ratio. A most preferred catalyst for use in the present invention comprises a zeolite having the structure of zeolite beta. Zeolite beta, first described in U.S. Pat. No. 3,308,069, is characterized by a three-dimensional porous structure formed with three mutually intersecting twelve-membered-ring channel systems. Two of the channel systems are substantially linear, while the third channel system is nonlinear. This third, tortuous channel system is formed by the intersections of the two linear systems. Zeolite beta materials for use in the invention can be obtained from commercial sources or prepared using techniques known and reported in the art and industry. Zeolite beta materials currently available from commercial sources exhibit a constraint index of about 0.6 and a spaciousness index of about 18.

It will be understood that zeolite beta as used herein refers to all zeolites having the characteristic zeolite beta microstructure, including for example those described early on in U.S. Pat. No. 3,308,069, as well as the more crystalline zeolite beta materials later developed and described in U.S. Pat. Nos. 4,923,690 and 5,164,169. The crystal sizes of these zeolites can vary widely, for example ranging from 0.01 to 3 microns. In this regard, these values for crystal size are determined by conventional scanning electron microscopy or transmission electron microscopy, wherein the minimum crystal size is taken as the dimension of a reference. This assay is disclosed in greater detail in U.S. Pat. No. 4,828, 679, to which reference may be made for additional information.

As indicated above, the zeolite catalyst selected for use in the invention may optionally incorporate one or more metals. Such catalysts can be prepared by effectively modifying the parent zeolite material through treatment with one or more metal ions or compounds containing the same. These metal ions include, for example, ions of the transition metals, for instance, tungsten, zinc, tin, thallium, lead, cobalt, cadmium, copper, nickel, platinum, palladium, gallium, nickel, rhodium, and iridium. This treatment may be carried out in any number of ways known in the art and may be carried out several times if desired to ensure substantial metal uptake on the zeolite.

For example, a preferred method of treatment is to add the zeolite to an aqueous solution of the desired metal ion or compound in stoichiometric excess and then to heat the mixture for some time at a predetermined temperature accompanied by stirring. The metal ions or compounds used are provided in the form of water soluble salts such as ammonium, nitrate, halide or acetate salts. This is followed by filtering, rinsing and drying, and then calcining at elevated temperature to obtain the finished catalyst. An alternate or possible further procedure is to prepare a physical mixture of the zeolite and the desired salt either dry or in the presence of enough water to constitute a paste or similar consistency, and then to complete the modification by blending or other suitable physical means. These and other similar procedures known in the art are all within the scope of the invention.

As a result of this treatment procedure, an effective amount of the metal is taken up in the zeolite structure. The amount and method of this uptake will vary depending on many factors such as the identity and concentration of reactants, the specific treatment procedures and the like, all of which are within the skill of those experienced in this area to select and to control. The same are therefore within the scope of the invention so long as the characteristics described herein are met. Nevertheless, concentrations up to about 1.0 mg equivalent/g of the selected metal in the modified catalyst are obtainable and may be desired in a given circumstance. Similarly, no particular method of uptake is required with physical absorption, adsorption and other forces coming into play and with chemical means such as ion-exchange and the like also occurring with given reactants exposed to certain treatment procedures. In any case, the treatment procedure may occur before or after the zeolite is formulated with a catalyst matrix or binder, as discussed further below.

As previously discussed, the processes of the present invention may involve a broad range of bases syntheses known or developed for the production of pyridine and/or its alkylpyridine derivatives. Generally speaking, the preferred reactants used in the present invention include $C_1$–$C_5$ aliphatic aldehydes which can be saturated or unsaturated, and/or $C_3$–$C_5$ aliphatic ketones which likewise can be saturated or unsaturated, which are reacted in admixture with ammonia. The organic reactants can be used alone or in admixture with one another, with the primary pyridine base product or products depending upon the selected combination of reactants and their relative amounts, as is well known in the pyridine and related industries. As well, the organic reactants can be provided and used in monomeric, oligomeric (e.g. dimers and trimers) and polymeric form. As an example, formaldehyde may be fed to the reaction in the form of formalin, paraformaldehyde or sym-trioxane and acetaldehyde as paraldehyde. Other compatible feed components, for example alkanols such as methanol, may also be used in the reaction, which further is preferably conducted in the absence of air or other sources of oxygen gas.

The following Table provides an illustrative list of some of the known reactant/product combinations for pyridine base syntheses. As those skilled in the pertinent field will understand, reactants and their ratios used will vary significantly according to many factors, not the least of which is the base synthesis process at hand and the particular pyridine or alkylpyridine base product yield or ratio sought to be achieved.

TABLE

| Feed Components + $NH_3$ | Intended Major Products |
| --- | --- |
| Acetaldehyde/Formaldehyde | Pyridine + β-Picoline |
| Acetaldehyde/Formaldehyde/ Propionaldehyde | β-Picoline |
| Acetaldehyde/Formaldehyde/ Acetone | α-Picoline |
| Acetaldehyde/Formaldehyde/ Methylethylketone | 2-Ethylpyridine + 2,3-Lutidine |
| Acetaldehyde/Formaldehyde/ Butyraldehyde | 3-Ethylpyridine |
| Acetaldehyde/Formaldehyde/ 3-Pentanone | 2-Ethyl-3-methylpyridine |
| Acetaldehyde/Acetone | 2,4,6-Collidine + 2,4-Lutidine |
| Acetaldehyde | α-Picoline + γ-Picoline |

TABLE-continued

| Feed Components + $NH_3$ | Intended Major Products |
| --- | --- |
| Formaldehyde/Acetone | 2,6-Lutidine |
| Formaldehyde/Acetone/ Propionaldehyde | 2,5-Lutidine |
| Formaldehyde/Propionaldehyde | 3,5-Lutidine |
| Acrolein | β-Picoline + Pyridine |
| Crotonaldehyde/Acetone | 2,4-Lutidine |
| Propionaldehyde | α-Parvoline |

It is understood that all such base synthesis processes and reactant and product combinations are suitable and within the scope of the invention. Similarly, the reaction conditions such as the molar amounts, temperatures and times used and the appropriate equipment and procedures such as the desirability of pre-mixing or of operating in an inert environment will likewise vary and are well within the skill and knowledge of those practiced in this area. For example, for the pyridine-beta synthesis it is generally preferred that a feed of formaldehyde to acetaldehyde in a mole ratio of at least about 1:1 is used. The addition of methanol to the extent of about 5 to 70% of the formaldehyde component is also preferred, as originally described in U.S. Pat. No. 2,807,618. Water can be present in the formaldehyde feed as desired to provide a stable, storable solution.

Ammonia is preferably supplied in a ratio of at least about 0.6:1 to the total organic components in the feed, with a range of about 0.7 to 5 being more preferred and about 0.8 to 3.5 being most preferred for the majority of pyridine base synthesis reactions. In a fluid bed process, the feed rate is in turn chosen to give good fluidization of the bed, usually in the range of a superficial velocity between about 0.3 to 4.0 ft./sec. Temperature of the reaction is preferably between about 350° C. and 550° C., more preferably between about 400° C. and 500° C. The products of the reaction are condensed and separated into pure compounds by drying and distillation as is well known in the art.

As mentioned previously, the base synthesis processes of the invention can be carried out in any suitable reaction system including both fixed bed and moving or mobilized (e.g. fluidized) bed arrangements. In this regard, pure zeolites are commonly in the form of very fine powders preferable neither for fixed- or fluid-bed usage. The zeolite powders are typically incorporated into a binder or matrix and then pelletized or extruded (for a fixed-bed catalyst) or ground or spray-dried (for a fluid-bed catalyst) to produce a form having commercial application. Such binders can be conventional and typically include, for example, naturally-occurring or synthetic materials such as clays (e.g. kaolin or montmorillonite), silica, alumina, silica-alumina, silica-magnesia, silica-zirconia, and ternary compositions such as silica-aluminal-thoria, silica-alumina-zirconia, silica-alumina-magnesia, silica-magnesia-zirconia, and the like. As to amounts, the amount of binder (when used) in the formulated catalyst material will usually be up to about 80% w/w relative to the zeolite. Especially for fluidized-bed operation, the resulting catalyst material will preferably have a particle size of about 5–500 μm, with an average particle size on the order of 60–100 μm being preferred.

For use in the present invention, a fluid-bed reactor and catalyst is expected to be preferred in order to also achieve the expected higher yields and ease of regeneration and use characteristic of such systems. The equipment set up and operation of fluid-bed reactors vary according to many factors tied to the particular reaction under consideration. The same are readily constructed by those of ordinary skill in the art, and are all within the scope of the invention herein. Reaction parameters such as temperature, feed mole ratios, feed velocity and contact time and the like vary over a wide range of operable conditions also well known and within the scope of the invention.

The following specific Examples are given in further explanation and description of the embodiments of the invention and are meant to be exemplary and not limitations thereof. The yields reported in the Tables below were caculated as Yield of Compound(s)=(weight of pyridine compound(s) formed)/(weight of liquid feed delivered excluding water). The Productivities reported are based on either catalyst weight (g/g cat/h) or bed volume (g/L/h). The reported product ratios are weight ratios, and the β-purity= (weight of beta-picoline)×100/(weight of beta-picoline+ gamma-picoline). The following abbreviations are used: HOS=hours on stream; PP=pyridine productivity; CT=contact time; Regen of=regenerated catalyst of; org= organic feeds; Pyr=pyridine; Pic=picolines; β=β-picoline; Lut=lutidine; Parv=α-parvaline; Coll=collidine; 2-Et-3- Me=2-ethyl-3-methylpyridine; MEK=methylethylketone; Etpyr=ethylpyridine; T=temperature; M=metal; Prod= productivity; Conv=conversion; Cat=catalyst; LHSV=liquid hourly space velocity; TMB=trimethylbenzene.

EXAMPLES 1–15

A series of base synthesis reactions was carried out in a microreactor to produce primarily pyridine and β-picoline. Each run utilized 4 cm$^3$ of catalyst having a particle size range of 0.5–1.0 mm diameter. The catalyst bed was immobilized in a quartz tube held in place by two plugs of silica wool. A standard feed (acetaldehyde and formaldehyde in a 1:1 mole ratio, with the formaldehyde originating from a mixture containing 45% formaldehyde, 10% methanol and the remainder water) was used for all of the runs in this Example with an ammonia/organic mole ratio of about 1.2. Prior to reaction, the catalyst was activated (or regenerated in the case of catalyst reuse) at 550° C. overnight (18 hours) in flowing air, followed by nitrogen gas flow for 10 minutes at 480° C. to flush the reactor unit. Anhydrous, gaseous ammonia was introduced at a rate of 40 cm$^3$ min$^{-1}$ beginning approximately 10 minutes before the flow of liquid feed was started. Three samples were collected during a five hour run at 2.0, 3.0, and 5.0 hours-on-stream ("HOS") at 480° C. (contact time 1 sec.) representing 1.5, 2.5, and 4.0 HOS as mid-points of the test periods. The collected liquid samples were homogenized with methanol before adding a known amount of 3-pentanone as a standard. The sample was then analyzed by GC using standard techniques. After completion of the run, the unit was flushed with nitrogen gas and the catalyst initially regenerated at 500° C. in 20% air/80% nitrogen gas for 30 minutes. The temperature was then increased to 550° C. and the proportion of air to nitrogen gas increased in stages until the catalyst was under a 100% atmosphere of air.

The zeolites used, mordenites (Tosoh Corp.), zeolite-L (PQ Corp.), zeolite-beta (PQ Corp.) and Ultrastable-Y (Tosoh Corp.) were provided either as the H$^+$ or NH$_4^+$-forms, and bound with about 20–50% w/w silica (Ludox AS-40, Du Pont Chemical Co.) to provide an effective catalyst for the reactions. Calcination (550° C.) converted the NH$_4^+$-forms to the H$^+$-form. The resulting cakes were crushed and sieved with the 0.50–1.00 mm size range being collected. The following listing shows catalyst weights (4 cm$^3$ bed loading, 0.50–1.00 mm), abbreviations and some pertinent physical data on the zeolite catalysts used in these Examples.

| H$^+$-Zeolite | SiO$_2$/Al$_2$O$_3$ Ratio | Abbrev. | % SiO$_2$ Binder | 4 cm$^3$ Wt/g |
|---|---|---|---|---|
| Mordenite | 16 | MOR(16) | 30% | 2.04 |
| Mordenite | ≧100 | MOR(100) | 50% | 1.76 |
| Zeolite-Beta | 25 | BEA | 20% | 1.54 |
| Zeolite-L | 6 | LTL | 20% | 1.90 |
| Ultrastab.-Y | ≧100 | USY | 50% | 2.65 |

Table 1 sets forth selected data for the base synthesis using the different zeolites. As can be seen, the zeolite beta catalyst provided dramatic and unexpected results in the base synthesis process, providing a high and consistent pyridine productivity in the range of about 0.5 g/g cat/hour and about 180 to 200 g/L/h. These results far outdistance the results obtained with the other large pore zeolites tested, including mordenite and zeolite-L. Mordenite is known to have a 2-dimensional (2-D) channel system with intersecting 8-member-ring and 12-member-ring channels. Although the present invention is not limited by any theory, it is believed that the 8-member-ring channels may be too small for acetaldehyde and pyridine bases to diffuse through. This being the case, it may be a combination of slow or limited mass transfer along the 12-member-ring channels and pore blockage through coking which lead to the poor performance.

Zeolite-L is a unidimensional large pore zeolite with an aperture of 7.1 Å, and also gave poor results in this testing. Zeolite-L is typically synthesized with a silica to alumina ratio of 5–7 from a gel containing potassium ions.

On the other hand, Table 1 shows that the zeolite beta catalyst (BEA) gave an excellent yield and productivity of pyridine products with little deactivation over the run period. The pyridine productivity from BEA was about 0.46–0.52 g/g cat/h, vastly superior to any of the other large pore zeolites tested. In addition, two further runs were conducted and the performance of zeolite beta examined at different temperatures (450°–530° C.) and contact times. Table 2 sets out the results from these further runs, which show that in the applicant's work zeolite beta exhibited an optimal yield/productivity for pyridine products at about 480° C. In addition, the high % β-purity obtained is advantageous for recovery of β-picoline by distillation for subsequent use.

The microstructure of zeolite beta was recently published by two independent groups of workers (J. B. Higgins et al., Zeolites, 8, 446, (1988); M. M. J. Treach et al., Nature, 332, 249, 1988). Zeolite beta is a three-dimensional (3-D) large pore zeolite (12-member rings) with elliptical apertures with approximate dimensions of 7.5×5.7 Å, and in the present invention these multidimensional large pores or channels are thought to permit high mobility of the reactants and products of the base synthesis reaction into and out of the zeolite beta microstructure. In contrast, the microstructures of mordenite and zeolite-L are effectively unidimensional or contain pores of dimensions which are innefective in the processes at hand (e.g. the 8-member ring pores of mordenite).

TABLE 1

| Zeolite | Ex. | HOS | Yield Pyr + Pics | PP g/g/h | PP g/L/h | Pyr/β | Pyr/Pic | % β-Purity | Notes |
|---|---|---|---|---|---|---|---|---|---|
| MOR(100) | 1 | 1.50 | 0.115 | 0.12 | 52 | 1.62 | 1.47 | 96.3 | |
| | | 2.50 | 0.112 | 0.12 | 52 | 1.63 | 1.51 | — | |
| | | 4.00 | 0.109 | 0.11 | 48 | 1.55 | 1.34 | 95.5 | |
| MOR(16) | 2 | 1.50 | 0.122 | 0.11 | 56 | 1.58 | 1.51 | — | |
| | | 2.50 | 0.137 | 0.13 | 64 | 1.64 | 1.57 | — | |
| | | 4.00 | 0.141 | 0.13 | 67 | 1.73 | 1.65 | — | |
| LTL | 3 | 1.50 | 0.086 | 0.08 | 39 | 1.49 | 1.41 | — | |
| | | 2.50 | 0.078 | 0.07 | 35 | 1.39 | 1.39 | — | |
| | | 4.00 | 0.086 | 0.08 | 39 | 1.45 | 1.38 | — | |
| USY | 4 | 0.5 | 0.212 | 0.14 | 95 | 2.11 | 1.38 | 96.9 | |
| | | 2.50 | 0.217 | 0.17 | 115 | 2.29 | 2.16 | 97.5 | |
| | | 4.00 | 0.209 | 0.17 | 111 | 2.36 | 2.21 | 97.4 | |
| | 5 | 1.50 | 0.233 | 0.19 | 125 | 2.40 | 2.23 | 97.2 | Regen of 4. |
| | | 2.50 | 0.221 | 0.18 | 117 | 2.33 | 2.19 | 97.3 | |
| | | 4.00 | 0.195 | 0.16 | 104 | 2.33 | 2.19 | 97.3 | |
| BEA | 6 | 1.50 | 0.383 | 0.51 | 196 | 2.08 | 1.95 | 97.6 | |
| | | 2.50 | 0.378 | 0.50 | 193 | 2.04 | 1.93 | 97.6 | |
| | | 4.00 | 0.356 | 0.48 | 184 | 2.10 | 1.99 | 98.0 | |
| | 7 | 1.50 | 0.396 | 0.52 | 200 | 2.01 | 1.88 | 97.4 | Regen of 6. |
| | | 2.50 | 0.386 | 0.51 | 197 | 2.04 | 1.93 | 97.7 | |
| | | 4.00 | 0.347 | 0.46 | 178 | 2.07 | 1.96 | 97.9 | |

TABLE 2

| Ex. | Bed T (°C.) | HOS | Yield Pyr + Pics | PP g/g/h | PP g/L/h | Pyr/β | Pyr/Pic | % β-Purity | Notes |
|---|---|---|---|---|---|---|---|---|---|
| 6 | 480 | 1.50 | 0.383 | 0.51 | 196 | 2.08 | 1.95 | 97.6 | |
| | | 2.50 | 0.378 | 0.50 | 193 | 2.04 | 1.93 | 97.6 | |
| | | 4.00 | 0.356 | 0.48 | 184 | 2.10 | 1.99 | 98.0 | |
| 7 | 480 | 1.50 | 0.396 | 0.52 | 200 | 2.01 | 1.88 | 97.4 | Regen of 6. |
| | | 2.50 | 0.386 | 0.51 | 197 | 2.04 | 1.93 | 97.7 | |
| | | 4.00 | 0.347 | 0.46 | 178 | 2.07 | 1.96 | 97.9 | |
| 8 | 450 | 1.50 | 0.370 | 0.48 | 185 | 1.94 | 1.85 | 97.5 | Regen of 7. |
| | | 2.50 | 0.369 | 0.48 | 184 | 1.89 | 1.80 | 97.7 | |
| | | 4.00 | 0.353 | 0.46 | 175 | 1.88 | 1.78 | 97.7 | |
| 9 | 510 | 1.50 | 0.375 | 0.50 | 190 | 2.06 | 1.91 | 97.7 | Regen of 8. |
| | | 2.50 | 0.362 | 0.48 | 188 | 2.11 | 1.97 | 97.6 | |
| | | 4.00 | 0.332 | 0.45 | 173 | 2.19 | 2.06 | 97.8 | |
| 10 | 480 | 1.50 | 0.384 | 0.50 | 193 | 1.97 | 1.86 | 97.9 | Regen of 9. |
| | | 2.50 | 0.371 | 0.49 | 186 | 1.99 | 1.88 | 97.8 | |
| | | 4.00 | 0.335 | 0.45 | 173 | 2.13 | 2.03 | 98.1 | |
| 11 | 530 | 1.50 | 0.356 | 0.47 | 180 | 2.05 | 1.88 | 97.5 | Regen of 10. |
| | | 2.50 | 0.331 | 0.45 | 171 | 2.17 | 2.01 | 97.5 | |
| | | 4.00 | 0.302 | 0.41 | 159 | 2.31 | 2.15 | 97.6 | |
| 12 | 480 | 1.50 | 0.348 | 0.45 | 177 | 2.03 | 1.91 | 98.0 | Fresh. |
| | | 2.50 | 0.357 | 0.46 | 182 | 2.06 | 1.94 | 97.8 | |
| | | 4.00 | 0.352 | 0.46 | 181 | 2.08 | 1.97 | 97.9 | |
| 13 | 480 | 1.50 | 0.368 | 0.48 | 188 | 2.06 | 1.93 | 97.8 | Regen of 12. |
| | | 2.50 | 0.372 | 0.48 | 190 | 2.07 | 1.96 | 98.0 | |
| | | 4.00 | 0.359 | 0.47 | 187 | 2.19 | 2.07 | 97.8 | |
| 14 | 480 | 1.50 | 0.366 | 0.47 | 187 | 2.05 | 1.95 | 98.2 | Regen of 13. |
| | | 2.50 | 0.363 | 0.47 | 185 | 2.04 | 1.94 | 98.2 | |
| | | 4.00 | 0.343 | 0.47 | 176 | 2.08 | 1.97 | 98.2 | |
| 15 | 480 | 1.50 | 0.321 | 0.21 | 82 | 2.34 | 1.96 | 92.6 | Regen of 14; contact time = 2 seconds. |
| | | 2.50 | 0.330 | 0.22 | 85 | 2.32 | 1.97 | 92.8 | |
| | | 4.00 | 0.352 | 0.23 | 91 | 2.40 | 2.03 | 92.3 | |

EXAMPLES 16-26

In these Examples, various base synthesis reactions were carried out in a microreactor as described in Examples 1-15. Again, prior to reaction, the catalyst was activated/regenerated at 550° C. overnight (18 hours) in flowing air followed by nitrogen gas flow for 10 minutes at 10° C. below the reaction temperature. Anhydrous ammonia was introduced at the specified flow rate for another 10 minutes before the liquid feeds were introduced.

Liquid samples were collected at specified times with the reported HOS representing the mid-points of each test period. The samples were homogenized with methanol and analyzed by GC using n-butanol as a standard. After the completion of the runs, the unit was flushed with nitrogen gas and the catalyst initially regenerated at 500° C. in 20% air/80% nitrogen gas for 30 minutes. The temperature was then increased to 550° C. and the proportion of air to nitrogen gas increased in stages until the catalyst was under a 100% atmosphere of air.

The BEA was received as a NH$_4^+$-form and bound with 20% w/w silica. Subsequent calcination of BEA converted it to the H$^+$-form. The resulting cakes of catalyst were crushed and sieved to collect the 0.5–1.0 mm diameter of particle size.

2.6-Lutidine Reaction (Acetone/Formaldehyde).

Table 3 shows microreactor data (2 runs) for BEA at non-optimized run conditions, namely: 480° C., 1.5 seconds contact time, formaldehyde/acetone molar ratio=0.5 and ammonia/organic molar ratio=1.0. The 2,6-/2,4-lutidine and 2,6-lutidine/2,4,6-collidine ratios in Table 3 reveal that zeolite beta imposes definite shape selectivity effects on the 2,6-lutidine reaction. The catalyst gave relatively steady 2,6-/2,4-lutidine ratios with an average of 23. The average 2,6-lutidine/2,4,6-collidine ratio was 42.

Table 5 shows microreactor data obtained for the formation of 2Et3Mepyr at 480° C., 1.8 seconds contact time, acetaldehyde/3-pentanone molar ratio=1, formaldehyde/acetaldehyde molar ratio=1.1 and ammonia/organic molar ratio=0.8.

TABLE 3

| Cat. | Ex. | HOS | % Conv Me$_2$CO | Yield 2,6-Lut | 2,6-Lut Prod (g/g/h) | 2,6-Lut Prod (g/L/h) | 2,6-Lut/ 2,4,6-Coll | 2,6-Lut/ 2,4-Lut | Notes |
|---|---|---|---|---|---|---|---|---|---|
| BEA | 16 | 0.63 | 94.7 | 0.226 | 0.43 | 168 | 36 | 23 | Virgin |
|  |  | 1.50 | 93.7 | 0.263 | 0.53 | 208 | 38 | 21 |  |
|  |  | 2.50 | 92.6 | 0.247 | 0.49 | 195 | 44 | 19 |  |
|  | 17 | 0.63 | 95.2 | 0.224 | 0.49 | 194 | 44 | 29 | Regen of 16 |
|  |  | 1.50 | 92.7 | 0.289 | 0.54 | 214 | 45 | 25 |  |
|  |  | 3.00 | 91.3 | 0.250 | 0.52 | 205 | 43 | 22 |  |

3,5-Lutidine Reaction (Propionaldehyde/Formaldehyde)

Microreactor runs were carried out to evaluate the zeolite beta catalyst for the production of 3,5-lutidine from propionaldehyde and formaldehyde. Table 4 shows microreactor data (2 runs) at 450° C., 1.5 seconds contact time, propionaldehyde/formaldehyde molar ratio=0.5 and ammonia/organic molar ratio=1. The data for 3,5-lutidine production demonstrate that zeolite beta is advantageous in this reaction as well.

TABLE 4

| Cat | Ex. | HOS | % EtCHO conv. | Yield Pyr + Pics | Yield 3,5-Lut | 3,5-Lut Prod (g/g/h) | 3,5-Lut Prod (g/L/h) | 3,5-Lut/ (α-Parv + 2,3,5-Coll) | Notes |
|---|---|---|---|---|---|---|---|---|---|
| BEA | 18 | 0.50 | 99.2 | 0.012 | 0.413 | 0.89 | 346 | 24 | Virgin |
|  |  | 1.50 | 98.7 | 0.012 | 0.417 | 0.90 | 349 | 29 |  |
|  |  | 2.50 | 99.4 | 0.011 | 0.446 | 0.96 | 373 | 32 |  |
|  | 19 | 0.63 | 99.3 | 0.013 | 0.446 | 0.99 | 382 | 28 | Regen of 18 |
|  |  | 1.50 | 99.3 | 0.013 | 0.429 | 0.93 | 360 | 31 |  |
|  |  | 3.00 | 99.2 | 0.012 | 0.421 | 0.91 | 353 | 34 |  |

2-Ethyl-3-Methylpyridine (3-Pentanone/Acetaldehyde/Formaldehyde)

A mixed feed of 3-pentanone (Et$_2$CO), acetaldehyde and formaldehyde was used to form 2-ethyl-3-methylpyridine.

TABLE 5

| Cat | Ex. | HOS | % Et$_2$CO Conv. | Yield Pyr + Pics | Yield 2-Et-3-Me | % Sel. 2-Et-3-Me | Prod 2-Et-3Me g/g cat/h | 2-Et-3-Me/ α-Parv |
|---|---|---|---|---|---|---|---|---|
| BEA | 20 | 0.67 | 88.1 | 0.159 | 0.110 | 17 | 0.23 | 2.14 |
|  |  | 1.50 | 84.1 | 0.165 | 0.118 | 19 | 0.24 | 2.12 |
|  |  | 2.50 | 82.3 | 0.163 | 0.118 | 20 | 0.24 | 2.16 |
|  |  | 4.00 | 76.4 | 0.165 | 0.114 | 20 | 0.23 | 2.10 |

2,3-Lutidine and 2-Ethylpyridine (Methylethylketone/Acetaldehyde/Formaldehyde)

The reaction of methylethylketone with acetaldehyde and formaldehyde was studied in the formation of 2,3-lutidine and 2-ethylpyridine. Table 6 shows microreactor data (2 runs) for the catalyst at 440° C., 1.7 seconds contact time, acetaldehyde/methylethylketone molar ratio=1.0, formaldehyde/acetaldehyde molar ratio=1.1 and ammonia/organic molar ratio=1.7.

TABLE 6

| Cat | Ex. | HOS | % MEK Conv. | Yield Pyr + Pics | Yield 2,3-Lut + 2-Etpyr | Prod. 2,3-Lut + 2-Etpyr g/g cat/h | 2,3-Lut/ 2-Etpyr | Notes |
|-----|-----|-----|------|-------|-------|------|-----|-------|
| BEA | 21 | 0.63 | 98.3 | 0.114 | 0.135 | 0.22 | 1.8 | Virgin |
|     |    | 1.50 | 97.3 | 0.125 | 0.140 | 0.22 | 2.1 | |
|     |    | 3.00 | 95.6 | 0.134 | 0.140 | 0.22 | 2.3 | |
|     | 22 | 0.63 | 97.8 | 0.128 | 0.147 | 0.23 | 1.8 | Regen of 21 |
|     |    | 1.50 | 97.0 | 0.121 | 0.141 | 0.23 | 2.2 | |
|     |    | 3.00 | 97.1 | 0.093 | 0.152 | 0.24 | 2.5 | |

2,4,6-Collidine Reaction (Acetone)

The formation of 2,4,6-collidine from acetone alone was carried out. Table 7 shows the results of these runs at 440° C., contact time=1.7 seconds, ammonia/organic molar ratio= 2.7. As shown in Table 7, as with all of the above pyridines reactions, BEA once again showed good conversion of the organic reactant, in this case acetone.

TABLE 7

| Cat | Ex. | HOS | % Conv. $Me_2CO$ | Yield 2,4,6-Coll | Prod 2,4,6-Coll g/g cat/h | 2,4,6-Coll/ (2,6-Lut + TMB) | Notes |
|-----|-----|-----|------|-------|-------|-------|-------|
| BEA | 23 | 0.63 | 99.5 | 0.026 | 0.04 | 0.17 | Virgin |
|     |    | 1.50 | 98.5 | 0.070 | 0.11 | 0.42 | |
|     |    | 3.00 | 97.9 | 0.108 | 0.16 | 0.77 | |
|     | 24 | 0.75 | 99.1 | 0.033 | 0.05 | 0.15 | Regen of 23 |
|     |    | 1.80 | 97.8 | 0.085 | 0.13 | 0.45 | |
|     |    | 3.35 | 97.8 | 0.113 | 0.17 | 0.77 | |

Pyr/β-Picoline Reaction from Acrolein

Table 8 shows microreactor data (2 runs) for the pyridine-β-picoline reaction using acrolein+water feed at 480° C., contact time=1.9 seconds, acrolein/water molar ratio= 1.0:0.35, ammonia/organic molar ratio=3.2.

TABLE 8

| Cat | Ex. | HOS | Yield Pyr + Pics | Pyr Prod. (g/g/h) | Pyr/β-Pic | Notes |
|-----|-----|-----|------|------|------|-------|
| BEA | 25 | 0.63 | 0.596 | 0.21 | 0.53 | Virgin |
|     |    | 1.50 | 0.564 | 0.18 | 0.47 | |
|     |    | 2.50 | 0.509 | 0.16 | 0.45 | |
|     |    | 4.00 | 0.422 | 0.12 | 0.40 | |
|     | 26 | 0.63 | 0.637 | 0.23 | 0.55 | Regen of 25 |
|     |    | 1.50 | 0.618 | 0.20 | 0.47 | |
|     |    | 2.50 | 0.581 | 0.18 | 0.45 | |
|     |    | 4.00 | 0.543 | 0.16 | 0.43 | |

EXAMPLES 27–75

These Examples describe base synthesis reactions conducted using catalysts incorporating a metal or metal oxide ($MO_x$) function. The 'bifunctional' $MO_x$/BEA catalysts were prepared by impregnation (i.e. metal nitrates), ion-exchange, wet-mixing (freshly precipitated metal hydroxide) and dry-mixing (commercial metal oxide). They were evaluated for the pyridine-beta- picoline reaction using a microreactor as described in Example 1, and utilized the same bed configuration, feed compositions, rates, and ratios. Unless otherwise noted, the metal loaded catalysts were prepared using BEA with a silica/alumina ratio of 25, hereinafter referred to as BEA(25).

In addition to the $MO_x$/BEA catalysts, BEA(25)/Silicalite (MFI) composite catalysts were also prepared and tested with the feed mix of Example 1. A sample of BEA with a silica to alumina ratio of 75, designated BEA(75), was also obtained from PQ Corporation and compared against the 'standard' BEA(25).

Catalyst Preparations

All catalysts, whether modified or not, were dried, calcined, and bound with 20% w/w silica, except Pt/BEA and Pd/BEA which were calcined at 350°–360° C. Furthermore, the metal or metal oxide was incorporated into the catalysts as follows. La/BEA was prepared by ion-exchange using an excess of $La(NO_3)_3 \cdot xH_2O$. Pb/BEA, Co/BEA, Cd/BEA and Zn/BEA were prepared by dissolving nitrates of the metals in water and precipitating the hydroxides with ammonium hydroxide. The precipitate was washed several times with distilled water and mixed with the support, dried (80° C.), calcined, and bound with Ludox AS-40. Sn/BEA was prepared with $Sn(OAc)_2$ in dilute HCl. Ga/BEA was prepared with $[Ga(H_2O)_6][NO_3]_3$ in hot water. Tl/BEA was prepared with $TlNO_3$ in hot water; Pt/BEA and Pd/BEA were prepared with $PdCl_2$ in water. W/BEA was prepared with $H_2WO_4$ in concentrated $NH_4OH$.

The above salts were dissolved in the indicated solvent. The resulting solutions were mixed with the BEA support, dried, calcined, and bound with Ludox AS-40. The nominal % weight $Mo_x$ of the catalysts were:

| Catalyst | % wt $Mo_x$ |
|----------|------|
| Pb/BEA | 2.4 |
| Co/BEA | 1.0 |

-continued

| Catalyst | % wt Mo$_x$ |
|---|---|
| Sn/BEA | 1.7 |
| Cd/BEA | 1.4 |
| Tl/BEA | 2.3 |
| Zn/BEA | 2.0 |
| W/BEA | 3.0 |

A zeolite beta/silicalite composite catalyst (MFI/BEA) was prepared by mixing dry samples of these catalyst powders well in equal proportions (50 wt %) with a mortar and pestle. The mixture was bound with silica, dried, and calcined as described above.

Results

Table 9 shows run data for metal and metal oxide promoted BEA(25) catalysts (MO$_x$/BEA). Each catalyst formulation was given a minimum of two runs (3–5 HOS) with 3–4 runs being more commonplace. All catalysts tested succesfully producted useful pyridine products, with certain catalysts giving lower yields on the first run but improved yields after regeneration, and other catalysts showing deterioration in activity after regeneration in the applicant's work. From these results, the preferred metals for modification of the zeolite catalysts include lead, cobalt, tin, cadmium, gallium, thallium and platinum.

BEA with different Silica/Alumina Ratios

Table 10 shows run data for BEA(75) compared alongside a repeat batch of BEA(25). BEA(75), like BEA5), performed surprisingly well in the base synthesis reaction.

Composite Catalyst

Shown in Table 10 are the results obtained from the testing of the composite catalyst. These results demonstrate that composite catalysts incorporating the zeolite beta along with other zeolites can effectively be used in the pyridine base synthesis.

TABLE 9

| M | Ex. | HOS | Yield Pyr + Pics | PP g/g/h | PP g/L/h | Pyr/β | Pyr/Pic | % β-Purity | Notes |
|---|---|---|---|---|---|---|---|---|---|
| H | 27 | 1.5 | 0.408 | 0.54 | 209 | 2.34 | 2.05 | 94.2 | Loading = 1.54 g |
|   |    | 2.5 | 0.401 | 0.54 | 206 | 2.36 | 2.06 | 94.0 |   |
|   |    | 4.0 | 0.397 | 0.52 | 201 | 2.29 | 2.00 | 93.7 |   |
|   | 28 | 1.5 | 0.406 | 0.54 | 209 | 2.38 | 2.07 | 94.2 | Regen of 27 |
|   |    | 2.5 | 0.389 | 0.52 | 201 | 2.41 | 2.11 | 94.2 |   |
|   |    | 4.0 | 0.374 | 0.50 | 192 | 2.35 | 2.05 | 93.8 |   |
|   | 29 | 1.5 | 0.386 | 0.52 | 200 | 2.41 | 2.12 | 94.8 | Regen of 28 |
|   |    | 2.5 | 0.395 | 0.53 | 205 | 2.42 | 2.15 | 94.7 |   |
|   |    | 4.0 | 0.380 | 0.51 | 198 | 2.40 | 2.14 | 94.8 |   |
| Pb | 30 | 1.5 | 0.412 | 0.55 | 216 | 2.52 | 2.19 | 94.3 | Loading = 1.58 g |
|   |    | 2.5 | 0.402 | 0.53 | 210 | 2.45 | 2.16 | 94.8 |   |
|   |    | 4.0 | 0.392 | 0.52 | 204 | 2.41 | 2.15 | 95.1 |   |
|   | 31 | 0.5 | 0.455 | 0.61 | 241 | 2.68 | 2.30 | 95.2 | Regen of 30 |
|   |    | 1.5 | 0.422 | 0.56 | 221 | 2.55 | 0.39 | 94.2 |   |
|   |    | 2.5 | 0.408 | 0.54 | 212 | 2.45 | 0.41 | 94.5 |   |
|   |    | 4.0 | 0.390 | 0.52 | 204 | 2.49 | 0.40 | 95.1 |   |
|   | 32 | 1.5 | 0.418 | 0.56 | 222 | 2.62 | 0.38 | 95.0 | Regen of 31 |
|   |    | 2.5 | 0.392 | 0.53 | 208 | 2.61 | 0.38 | 95.1 |   |
|   |    | 4.0 | 0.370 | 0.50 | 198 | 2.62 | 0.38 | 95.5 |   |
|   | 33 | 1.5 | 0.404 | 0.55 | 215 | 2.68 | 0.37 | 94.5 | Regen of 32 |
|   |    | 2.5 | 0.390 | 0.53 | 207 | 2.64 | 0.38 | 94.6 |   |
|   |    | 4.0 | 0.348 | 0.47 | 187 | 2.67 | 0.37 | 95.3 |   |
|   | 34 | 1.5 | 0.414 | 0.56 | 220 | 2.60 | 0.38 | 96.0 | Regen of 33 |
|   |    | 2.5 | 0.407 | 0.54 | 215 | 2.56 | 0.39 | 94.7 |   |
|   |    | 4.0 | 0.382 | 0.51 | 200 | 2.51 | 0.40 | 95.0 |   |
| Tl | 35 | 1.5 | 0.406 | 0.55 | 211 | 2.45 | 2.15 | 94.4 | Loading = 1.55 g |
|   |    | 2.5 | 0.406 | 0.54 | 210 | 2.36 | 2.10 | 94.9 |   |
|   |    | 4.0 | 0.418 | 0.56 | 215 | 2.33 | 2.08 | 94.7 |   |
|   | 36 | 1.5 | 0.416 | 0.55 | 214 | 2.41 | 2.08 | 92.5 | Regen of 35 |
|   |    | 2.5 | 0.402 | 0.53 | 206 | 2.34 | 2.07 | 94.5 |   |
|   |    | 4.0 | 0.395 | 0.53 | 204 | 2.35 | 2.08 | 94.6 |   |
|   | 37 | 1.5 | 0.409 | 0.55 | 213 | 2.47 | 2.15 | 94.2 | Regen of 36 |
|   |    | 2.5 | 0.408 | 0.54 | 209 | 2.34 | 2.06 | 94.2 |   |
|   |    | 4.0 | 0.384 | 0.51 | 199 | 2.39 | 2.11 | 94.5 |   |
|   | 38 | 1.5 | 0.370 | 0.50 | 193 | 2.49 | 2.17 | 94.2 | Regen of 37 |
|   |    | 2.5 | 0.388 | 0.51 | 199 | 2.37 | 2.06 | 93.8 |   |
|   |    | 4.0 | 0.390 | 0.51 | 197 | 2.25 | 1.98 | 94.1 |   |
| Sn | 39 | 0.6 | 0.406 | 0.58 | 215 | 2.31 | 2.18 | 97 | Loading = 1.47 g |
|   |    | 1.5 | 0.361 | 0.53 | 193 | 2.37 | 2.27 | 97 |   |
|   |    | 3.0 | 0.357 | 0.52 | 192 | 2.42 | 2.33 | 97 |   |
|   | 40 | 0.6 | 0.412 | 0.60 | 221 | 2.42 | 2.28 | 97 | Regen of 39 |
|   |    | 1.5 | 0.387 | 0.56 | 204 | 2.30 | 2.18 | 97 |   |
|   |    | 3.0 | 0.362 | 0.54 | 198 | 2.52 | 2.45 | 97 |   |
|   | 41 | 0.6 | 0.416 | 0.59 | 216 | 2.24 | 2.07 | 97.0 | Regen of 40 |
|   |    | 1.5 | 0.397 | 0.56 | 206 | 2.20 | 2.05 | 97.3 |   |
|   |    | 3.0 | 0.370 | 0.53 | 194 | 2.26 | 2.12 | 97.6 |   |
|   | 42 | 0.6 | 0.426 | 0.60 | 221 | 2.23 | 2.07 | 97.3 | Regen of 41 |
|   |    | 1.5 | 0.396 | 0.56 | 205 | 2.19 | 2.06 | 97.5 |   |
|   |    | 3.0 | 0.360 | 0.52 | 189 | 2.30 | 2.16 | 97.4 |   |
| Ga | 43 | 0.50 | 0.418 | 0.69 | 213 | 2.08 | 1.89 | 97.0 | Loading = 1.23 g |
|   |    | 1.25 | 0.392 | 0.66 | 202 | 2.15 | 1.97 | 96.9 |   |

TABLE 9-continued

| M | Ex. | HOS | Yield Pyr + Pics | PP g/g/h | PP g/L/h | Pyr/β | Pyr/Pic | % β-Purity | Notes |
|---|---|---|---|---|---|---|---|---|---|
| | | 2.75 | 0.362 | 0.62 | 191 | 2.29 | 2.12 | 97.1 | |
| | 44 | 0.59 | 0.396 | 0.65 | 201 | 2.06 | 1.88 | 97.1 | Regen of 43 |
| | | 1.50 | 0.389 | 0.65 | 200 | 2.14 | 1.97 | 97.0 | |
| | | 3.00 | 0.347 | 0.59 | 182 | 2.24 | 2.07 | 97.1 | |
| Cd | 45 | 0.63 | 0.404 | 0.57 | 211 | 2.23 | 2.08 | 98.5 | Loading = 1.48 g |
| | | 1.50 | 0.398 | 0.55 | 205 | 2.13 | 2.01 | 98.6 | |
| | | 3.00 | 0.381 | 0.53 | 197 | 2.11 | 2.03 | 98 | |
| | 46 | 0.63 | 0.429 | 0.60 | 222 | 2.19 | 2.04 | 98.3 | Regen of 45 |
| | | 1.50 | 0.402 | 0.56 | 208 | 2.14 | 2.05 | 98 | |
| | | 3.00 | 0.366 | 0.52 | 191 | 2.18 | 2.11 | 98 | |
| | 47 | 0.63 | 0.434 | 0.60 | 222 | 2.11 | 1.97 | 98.7 | Regen of 46 |
| | | 1.50 | 0.381 | 0.54 | 199 | 2.22 | 2.10 | 98.7 | |
| | | 3.00 | 0.364 | 0.52 | 192 | 2.24 | 2.16 | 98 | |
| | 48 | 0.63 | 0.384 | 0.54 | 199 | 2.17 | 2.05 | 98 | Regen of 47 |
| | | 1.50 | 0.389 | 0.55 | 202 | 2.16 | 2.07 | 98 | |
| | | 3.00 | 0.358 | 0.51 | 191 | 2.34 | 2.26 | 98 | |
| Co | 49 | 0.63 | 0.408 | 0.56 | 214 | 2.30 | 2.11 | 98.0 | Loading = 1.53 g |
| | | 1.50 | 0.392 | 0.53 | 204 | 2.22 | 2.07 | 98.3 | |
| | | 3.00 | 0.344 | 0.48 | 182 | 2.33 | 2.19 | 98.1 | |
| | 50 | 0.63 | 0.384 | 0.54 | 207 | 2.48 | 2.33 | 98.4 | Regen of 49 |
| | | 1.50 | 0.374 | 0.51 | 196 | 2.27 | 2.11 | 97.5 | |
| | | 3.00 | 0.347 | 0.47 | 181 | 2.21 | 2.09 | 98.2 | |
| | 51 | 0.63 | 0.422 | 0.59 | 225 | 2.35 | 2.24 | 98 | Regen of 50 |
| | | 1.50 | 0.381 | 0.52 | 199 | 2.24 | 2.11 | 98.5 | |
| | | 3.00 | 0.342 | 0.48 | 182 | 2.37 | 2.25 | 98.3 | |
| | 52 | 0.63 | 0.424 | 0.58 | 221 | 2.20 | 2.10 | 98 | Regen of 51 |
| | | 1.50 | 0.381 | 0.51 | 195 | 2.11 | 1.99 | 98.6 | |
| | | 3.31 | 0.340 | 0.47 | 179 | 2.30 | 2.18 | 98.6 | |
| La | 53 | 0.63 | 0.367 | 0.53 | 179 | 1.85 | 1.73 | 97.3 | Loading = 1.35 g |
| | | 1.50 | 0.330 | 0.47 | 160 | 1.83 | 1.71 | 97.1 | |
| | | 3.00 | 0.300 | 0.43 | 147 | 1.85 | 1.74 | 97.4 | |
| | 54 | 0.63 | 0.373 | 0.56 | 189 | 2.05 | 1.90 | 97.1 | Regen of 53 |
| | | 1.50 | 0.340 | 0.50 | 169 | 1.91 | 1.80 | 97.7 | |
| | | 3.00 | 0.312 | 0.46 | 156 | 1.92 | 1.83 | 98.1 | |
| W | 55 | 1.50 | 0.323 | 0.47 | 164 | 2.26 | 1.95 | 94.8 | Loading = 1.39 g |
| | | 2.50 | 0.186 | 0.27 | 95 | 2.39 | 2.02 | 94.0 | |
| | 56 | 1.50 | 0.311 | 0.47 | 163 | 2.52 | 2.16 | 94.6 | Regen of 55 |
| | | 2.50 | 0.270 | 0.41 | 142 | 2.56 | 2.20 | 95.3 | |
| | | 4.00 | 0.253 | 0.39 | 135 | 2.67 | 2.29 | 95.4 | |
| Zn | 57 | 1.50 | 0.342 | 0.50 | 182 | 2.70 | 2.33 | 94.3 | Loading = 1.45 g |
| | | 2.50 | 0.310 | 0.46 | 165 | 2.63 | 2.30 | 94.7 | |
| | | 4.00 | 0.275 | 0.40 | 146 | 2.62 | 2.29 | 94.9 | |
| | 58 | 0.80 | 0.364 | 0.50 | | 2.02 | 1.92 | 97.9 | Loading = 1.49 g |
| | | 1.50 | 0.315 | 0.43 | | 2.00 | 1.88 | 97.6 | |
| | | 3.00 | 0.282 | 0.39 | | 2.17 | 2.06 | 98.0 | |
| | 59 | 0.80 | 0.387 | 0.54 | | 2.12 | 2.01 | 98.2 | Regen of 58 |
| | | 1.50 | 0.326 | 0.45 | | 2.10 | 1.99 | 98.0 | |
| | | 3.10 | 0.287 | 0.40 | | 2.25 | 2.14 | 98.0 | |
| Pt | 60 | 0.63 | 0.399 | 0.58 | 206 | 2.21 | 1.99 | 96.6 | Loading = 1.43 g |
| | | 1.50 | 0.394 | 0.57 | 204 | 2.20 | 2.00 | 96.6 | |
| | | 3.00 | 0.384 | 0.56 | 201 | 2.24 | 2.06 | 96.8 | |
| | 61 | 0.63 | 0.369 | 0.53 | 190 | 2.16 | 1.96 | 96.6 | Regen of 60 |
| | | 1.50 | 0.374 | 0.54 | 192 | 2.13 | 1.96 | 96.8 | |
| | | 3.00 | 0.339 | 0.50 | 178 | 2.24 | 2.07 | 97.0 | |
| Pd | 62 | 0.63 | 0.356 | 0.50 | 188 | 2.42 | 2.13 | 95.0 | Loading = 1.50 g |
| | | 1.50 | 0.331 | 0.47 | 177 | 2.45 | 2.22 | 96.3 | |
| | | 3.00 | 0.294 | 0.43 | 160 | 2.56 | 2.35 | 96.8 | |
| | 63 | 0.63 | 0.383 | 0.53 | 201 | 2.32 | 2.07 | 95.6 | Regen of 62 |
| | | 1.50 | 0.377 | 0.51 | 193 | 2.08 | 1.92 | 96.9 | |
| | | 3.00 | 0.320 | 0.46 | 173 | 2.48 | 2.28 | 96.9 | |

TABLE 10

| H+-BEA | Ex. | HOS | Yield Pyr + Pics | PP g/g/h | PP g/L/h | Pyr/β | Pyr/Pic | % β-Purity | Notes |
|---|---|---|---|---|---|---|---|---|---|
| BEA(75) | 64 | 0.63 | 0.387 | 0.51 | 201 | 2.14 | 1.99 | 97.5 | Loading = 1.57 g |
| | | 1.50 | 0.372 | 0.50 | 197 | 2.24 | 2.08 | 97.1 | |
| | | 3.00 | 0.379 | 0.51 | 201 | 2.24 | 2.09 | 97.0 | |
| | 65 | 0.63 | 0.372 | 0.50 | 194 | 2.16 | 2.00 | 97.1 | Regen of 64 |
| | | 1.50 | 0.377 | 0.51 | 200 | 2.27 | 2.11 | 96.7 | |
| | | 3.00 | 0.356 | 0.48 | 189 | 2.26 | 2.11 | 96.9 | |
| | 66 | 0.63 | 0.383 | 0.51 | 201 | 2.18 | 2.03 | 97.3 | Regen of 65 |

TABLE 10-continued

| H+-BEA | Ex. | HOS | Yield Pyr + Pics | PP g/g/h | PP g/L/h | Pyr/β | Pyr/Pic | % β-Purity | Notes |
|---|---|---|---|---|---|---|---|---|---|
|  |  | 1.50 | 0.373 | 0.50 | 195 | 2.15 | 2.01 | 97.0 |  |
|  |  | 3.00 | 0.360 | 0.49 | 191 | 2.28 | 2.13 | 97.1 |  |
| BEA(25) | 67 | 0.63 | 0.412 | 0.54 | 210 | 2.01 | 1.87 | 97.3 | Loading = 1.58 g |
|  |  | 1.50 | 0.377 | 0.50 | 195 | 2.10 | 1.95 | 97.1 |  |
|  |  | 3.00 | 0.365 | 0.49 | 192 | 2.20 | 2.05 | 96.9 |  |
|  | 68 | 0.63 | 0.392 | 0.52 | 204 | 2.15 | 1.99 | 97.2 | Regen of 67 |
|  |  | 1.50 | 0.388 | 0.51 | 199 | 2.04 | 1.90 | 97.3 |  |
|  |  | 3.00 | 0.355 | 0.48 | 186 | 2.20 | 2.05 | 96.9 |  |
|  | 69 | 0.63 | 0.377 | 0.50 | 196 | 2.15 | 1.99 | 97.3 | Regen of 68 |
|  |  | 1.50 | 0.368 | 0.49 | 192 | 2.15 | 2.00 | 97.2 |  |
|  |  | 3.00 | 0.386 | 0.52 | 204 | 2.22 | 2.07 | 97.1 |  |
|  | 70 | 0.63 | 0.376 | 0.50 | 195 | 2.15 | 1.98 | 96.9 | Regen of 69 |
|  |  | 1.50 | 0.362 | 0.48 | 188 | 2.14 | 1.98 | 96.9 | (NH$_3$/org = 2.00) |
|  |  | 3.00 | 0.351 | 0.47 | 182 | 2.10 | 1.95 | 96.8 |  |
|  | 71 | 0.63 | 0.384 | 0.77 | 300 | 2.14 | 1.99 | 97.1 | Regen of 70 |
|  |  | 1.50 | 0.361 | 0.73 | 283 | 2.14 | 2.02 | 97.1 | (CT = 0.6 sec, |
|  |  | 2.50 | 0.345 | 0.70 | 273 | 2.18 | 2.07 | 97.5 | LHSV = 1.5) |
| MFI/BEA(25) | 72 | 0.50 | 0.428 | 0.48 | 222 | 2.30 | 2.12 | 96.6 | Loading = 1.87 g |
|  |  | 1.50 | 0.393 | 0.43 | 199 | 2.14 | 1.96 | 95.7 |  |
|  |  | 2.50 | 0.366 | 0.40 | 188 | 2.24 | 2.06 | 96.0 | T = 450° C. |
|  |  | 4.00 | 0.328 | 0.36 | 167 | 2.13 | 1.97 | 96.6 |  |
|  | 73 | 0.63 | 0.433 | 0.48 | 223 | 2.27 | 2.06 | 95.4 | Regen of 72 |
|  |  | 1.50 | 0.387 | 0.43 | 201 | 2.33 | 2.12 | 95.7 |  |
|  |  | 3.00 | 0.380 | 0.41 | 192 | 2.12 | 1.94 | 95.9 |  |
|  | 74 | 0.63 | 0.414 | 0.46 | 216 | 2.36 | 2.14 | 95.4 | Regen of 73 |
|  |  | 1.50 | 0.387 | 0.43 | 201 | 2.33 | 2.12 | 95.7 |  |
|  |  | 3.00 | 0.389 | 0.44 | 204 | 2.32 | 2.17 | 97.0 |  |
|  | 75 | 0.63 | 0.414 | 0.46 | 215 | 2.32 | 2.11 | 95.7 | Regen of 74 |
|  |  | 1.50 | 0.373 | 0.41 | 193 | 2.29 | 2.10 | 96.1 |  |
|  |  | 3.00 | 0.402 | 0.44 | 208 | 2.23 | 2.08 | 97.1 |  |

While the invention has been described in some detail in the foregoing description, the same is to be considered illustrative of the invention. It will be readily apparent to the skilled artisan that modifications and additions may be made to the procedures and materials described without departing from the spirit and scope of the invention. Such modifications and additions are therefore contemplated as being encompassed by the present invention.

What is claimed is:

1. A base synthesis process for the preparation of pyridine or its alkylpyridine derivatives comprising reacting one or more aldehydes and/or ketones or mixtures thereof containing from 1 to about 5 carbon atoms, with at least one reactant having more than 1 carbon atom, with ammonia in the gas phase and in the presence of an effective amount of a zeolite catalyst having a first dimension having channels formed by twelve-membered rings, and a second dimension having channels formed by ten- or twelve-membered rings, said zeolite catalyst having been prepared with a silica to alumina ratio of at least 15.

2. The process of claim 1 in which the organic reactants comprise one or more members selected from the group consisting of acetaldehyde, propionaldehyde, acetone, methylethylketone, butyraldehyde, and crotonaldehyde.

3. The process of claim 2 in which the organic reactants comprise acetaldehyde and formaldehyde, and comprising the additional step of recovering pyridine and beta-picoline as the products of said reacting.

4. The process of claim 3 in which the reactants also include methanol.

5. The process of claim 2 in which the zeolite as a constraint index less than 1 and a spaciousness index in the range of 10 to 20.

6. The process of claim 1 in which the reactant is acetaldehyde, and additionally comprising recovering alpha- and gamma-picoline as the products of said reacting.

7. The process of claim 1 in which the zeolite has the structure of zeolite beta.

8. The process of claim 1 in which the zeolite has been treated with a metal ion or compound.

9. The process of claim 1 in which the zeolite is in acidic form.

10. The process of claim 1, wherein the zeolite is formulated with a binder containing silica, alumina, or a combination thereof.

11. The process of claim 1 in which the reactants are a mixture of acetaldehyde, formaldehyde and propionaldehyde, and additionally comprising recovering pyridine and beta-picoline as the products of said reacting.

12. A catalyst for use in base synthesis processes for the preparation of pyridine or its alkylpyridine derivatives, comprising an effective amount of a zeolite catalyst having a silica to alumina molar ratio of at least 15, a first dimension having pores formed by twelve-membered rings, and a second dimension having pores formed by ten- or twelve-membered rings, said zeolite having been treated with one or more ions of or compounds containing lead, cobalt, tin, cadmium, gallium, thallium or platinum.

13. The catalyst of claim 12, which includes the zeolite and a binder containing silica, alumina, or a combination thereof.

14. The catalyst of claim 12, wherein the zeolite has the structure of zeolite beta.

15. The catalyst of claim 13, wherein the zeolite is zeolite beta.

16. A base synthesis process for preparing pyridine, or its alkylpyridine derivatives, comprising reacting one or more aldehydes, and/or ketones or mixtures thereof, containing from 1 to about 5 carbon atoms, with at least one reactant having more than 1 carbon atom, with ammonia in the gas phase and in the presence of an effective amount of a zeolite catalyst having the structure of zeolite beta.

17. The process of claim 16 in which the organic reactants comprise one or more members selected from the group consisting of acetaldehyde, propionaldehyde, acetone, methylethylketone, butyraldehyde, and crotonaldehyde.

18. The process of claim 17 in which the organic reactants comprise acetaldehyde and formaldehyde, and comprising the additional step of recovering pyridine and beta-picoline as the products of said reacting.

19. The process of claim 17 in which the reactants also include methanol.

20. The process of claim 18 in which the reactants also include methanol.

21. The process of claim 17 in which the reactant is acetaldehyde, and additionally comprising recovering alpha- and gamma-picoline as the products of said reacting.

22. The process of claim 16 in which the zeolite is in acidic form.

23. The process of claim 16 in which the zeolite has been treated with a metal ion or compound.

24. The process of claim 16, wherein the zeolite is formulated with a binder containing silica, alumina, or a combination thereof.

25. The process of claim 16 in which the reactants are a mixture of acetaldehyde, formaldehyde and propionaldehyde, and additionally comprising recovering pyridine and beta-picoline as the products of said reacting.

* * * * *

UNITED STATES PATENT AND TRADEMARK OFFICE
CERTIFICATE OF CORRECTION

PATENT NO. : 5,780,635
DATED : July 14, 1998
INVENTOR(S) : Colin H. McAteer et al.

It is certified that error appears in the above-indentified patent and that said Letters Patent is hereby corrected as shown below:

In col. 9, line 12, please add "%" in between the words "the" and "β-purity=".

In cols. 11 and 12, Table 2, in the second line of the row labeled "Ex. 9" under the column entitled "PP g/L/h", please delete "188" and insert in lieu thereof —186—.

In cols. 11 and 12, Table 2, in the second line of the row labeled "Ex. 10" under the column entitled "PP g/L/h", please delete "186" and insert in lieu thereof —188—.

In cols. 15 and 16, Table 7, in the second line of the row labeled "Ex. 23" under the column entitled "% Conv. $Me_2CO$", please delete "98.5" and insert in lieu thereof —98.8—

UNITED STATES PATENT AND TRADEMARK OFFICE
CERTIFICATE OF CORRECTION

PATENT NO. : 5,780,635
DATED : July 14, 1998
INVENTOR(S) : Colin H. McAteer, et al It is certified that error appears in the above-indentified patent and that said Letters Patent is hereby corrected as shown below:

In cols. 15 and 16, Table 7, in the first line of the row labeled "Ex. 24" under the column entitled "2,4,6-Coll/(2,6-Lut + TMB)", please delete "0.15" and insert in lieu thereof —0.18—.

In col. 18, line 13, please delete "BEA5" and insert in lieu thereof —BEA(25)—.

In col. 21, line 60, the first line of claim 5, please delete "as" and insert in lieu thereof —has—.

Signed and Sealed this

Twelfth Day of October, 1999

Q. TODD DICKINSON

*Attest:*

*Attesting Officer*     Acting Commissioner of Patents and Trademarks